(12) United States Patent
Bhalla

(10) Patent No.: US 7,624,455 B1
(45) Date of Patent: Dec. 1, 2009

(54) STERILE GLOVE WITH TOUCHLESS DONNING

(76) Inventor: Jagmohan Bhalla, 2022 Columbia Rd., NW., #605, Washington, DC (US) 20009

( * ) Notice: Subject to any disclaimer, the term of this patent is extended or adjusted under 35 U.S.C. 154(b) by 0 days.

(21) Appl. No.: 12/138,546

(22) Filed: Jun. 13, 2008

(51) Int. Cl.
*A41D 19/00* (2006.01)
(52) U.S. Cl. .......................... 2/161.7; 2/160
(58) Field of Classification Search .............. 2/16, 2/17, 158, 159, 160, 161.7, 901, 161.6, 162, 2/910, 917; 128/856, 878, 879; 604/292; 223/111, 112; 602/21
See application file for complete search history.

(56) References Cited

U.S. PATENT DOCUMENTS

| | | | | |
|---|---|---|---|---|
| 2,041,254 A | * | 5/1936 | Lipshutz | 2/160 |
| 2,325,482 A | * | 7/1943 | Curran | 2/159 |
| 2,976,540 A | * | 3/1961 | Sutherland | 2/161.7 |
| 4,069,913 A | | 1/1978 | Harrigan | |
| 4,155,494 A | | 5/1979 | Poncy et al. | |
| 4,845,780 A | | 7/1989 | Reimers et al. | |
| 4,876,747 A | * | 10/1989 | Coffey et al. | 2/168 |
| 4,884,300 A | | 12/1989 | Vistins | |
| 4,898,309 A | | 2/1990 | Fischer | |
| 4,915,226 A | | 4/1990 | Keenan | |
| 4,971,233 A | | 11/1990 | Keenan | |
| 5,020,159 A | * | 6/1991 | Hellickson | 2/158 |
| 5,020,160 A | * | 6/1991 | Cano | 2/159 |
| 5,065,863 A | | 11/1991 | Moyet-Ortiz | |
| 5,365,608 A | | 11/1994 | Flick | |
| 5,398,344 A | * | 3/1995 | Hirano | 2/159 |
| 5,467,483 A | | 11/1995 | Saadatmanesh et al. | |
| 5,816,440 A | | 10/1998 | Shields et al. | |
| 5,864,883 A | * | 2/1999 | Reo | 2/158 |
| 5,864,885 A | * | 2/1999 | Grinberg | 2/160 |
| 6,375,034 B1 | | 4/2002 | Corbett | |
| 6,435,388 B1 | | 8/2002 | Binder et al. | |
| 6,442,761 B1 | | 9/2002 | Huang | |
| 7,051,378 B1 | * | 5/2006 | Mire | 2/161.7 |
| 7,246,382 B2 | | 7/2007 | Plut et al. | |
| 2005/0241046 A1 | | 11/2005 | Griesbach et al. | |
| 2006/0185059 A1 | | 8/2006 | Taha et al. | |
| 2008/0172767 A1 | * | 7/2008 | Friedstrom | 2/16 |

FOREIGN PATENT DOCUMENTS

GB PCT/GB2008/001721 * 11/2008

* cited by examiner

*Primary Examiner*—Gary L Welch
*Assistant Examiner*—Amber R Anderson
(74) *Attorney, Agent, or Firm*—Squire, Sanders & Dempsey, LLP

(57) ABSTRACT

A sterile glove includes a cuff that has an inside surface and an outside surface. The cuff is folded over at a fold when the glove is packaged and when it is initially removed from the package. The glove further includes a hand and finger portion. The glove further includes a detachable tab that is coupled to the cuff and includes a free end. The detachable tab is adapted to facilitate a donning of the glove before being detached.

17 Claims, 6 Drawing Sheets

STERILE GLOVE WITH TOUCHLESS DONNING

FIELD OF THE INVENTION

One embodiment is directed generally to a sterile glove, and in particular to a sterile glove that allows for touchless donning.

BACKGROUND INFORMATION

Sterile elastomeric gloves are used with increasing frequency by medical and laboratory professionals to prevent the tactile transfer of foreign materials during various procedures. Sterile gloves are typically packaged with their cuffs folded over to expose a portion of the inner surface of the cuff. This allows the gloves to be picked up and held during donning by touching only the area close to the fold and at some distance from the cuff rim, which minimizes the risk of contamination.

Various packaging and dispenser improvements and techniques have been introduced to address the problems of sterile glove donning. However, these known methods tend to unnecessarily increase the cost and complexity of use and manufacture of the gloves.

SUMMARY OF THE INVENTION

One embodiment is a sterile glove that includes a cuff that has an inside surface and an outside surface. The cuff is folded over at a fold when the glove is packaged and when it is initially removed from the package. The glove further includes a hand and finger portion. The glove further includes a detachable tab that is coupled to the cuff and includes a free end. The detachable tab is adapted to facilitate a donning of the glove before being detached.

DETAILED DESCRIPTION

One embodiment is a sterile glove with a detachable grasping means that allows the glove to be donned without touching any of the wearable portion of the glove.

Figure 1:
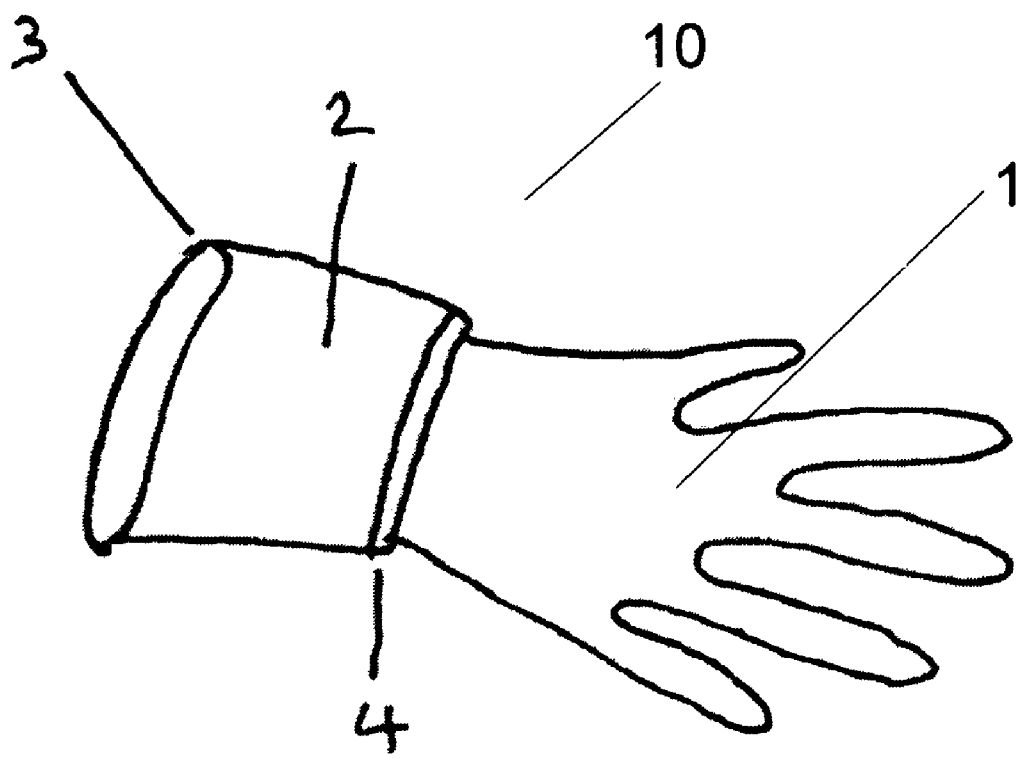
FIG. 1 is a perspective view of a prior art sterile glove as it is configured when it is removed from packaging and before being donned by a user.

FIG. 1 is a perspective view of a prior art sterile glove 10 as it is configured when it is removed from packaging and before being donned by a user. Glove 10 includes a cuff 2, a cuff rim 4, and finger and hand portion 1. Cuff 2 of glove 10 as shown in FIG. 1 is in a state of being folded over at fold 3 so that at least some of the inside surface is exposed. This allows glove 10 to be held by touching only the region of the folded over cuff 2 that is near fold 3 thereby limiting contact to an area at some distance from cuff rim 4 and reducing the risk of contamination. The folded over cuff is unfolded before use of the glove. Use of the glove can include any activity after the glove has been donned. "Donning" includes all activities involved in inserting the hand into the glove and in fully unfolding its cuff.

Figure 2:
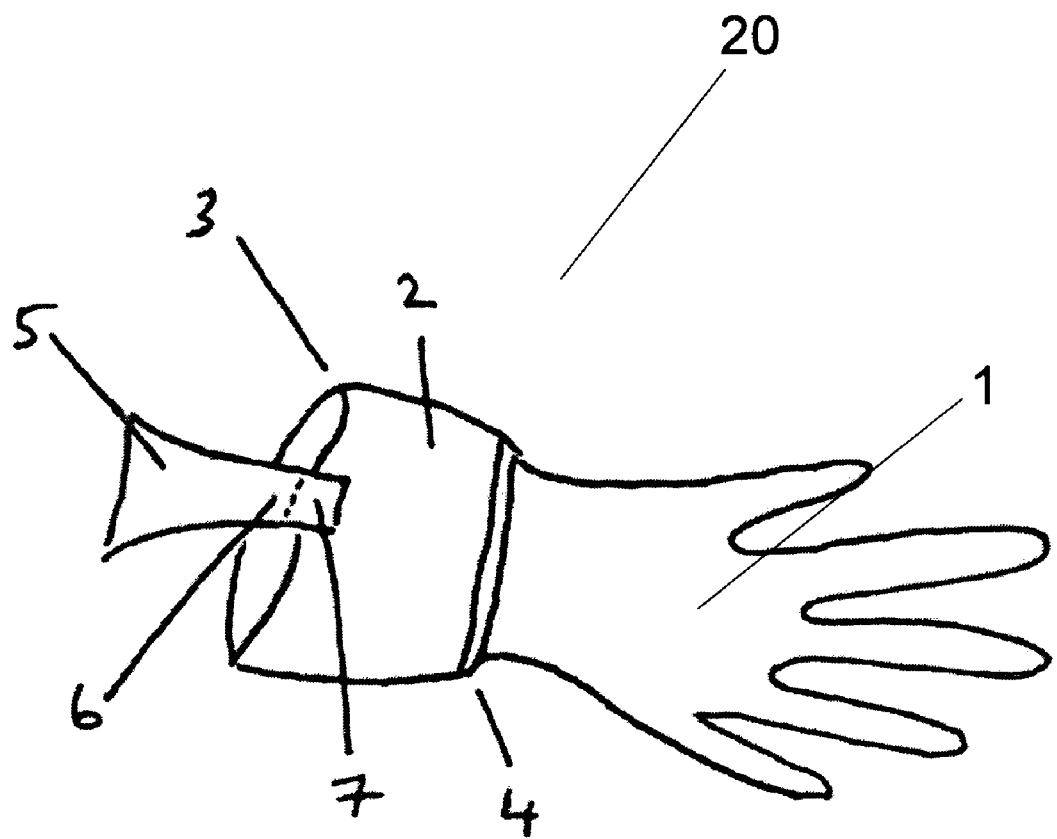
FIG. 2 is a perspective view of a sterile glove in accordance with one embodiment as it is configured when it is removed from packaging or other storage means and before being donned by a user.

FIG. 2 is a perspective view of a sterile glove 20 in accordance with one embodiment as it is configured when it is removed from its packaging or other storage means and before being donned by a user. As with glove 10, glove 20 includes a folded over cuff 2 that has a cuff rim 4 and is folded over at fold 3, and finger and hand portion 1. In its folded over state, the inside surface of cuff 2 is exposed. Glove 20 further includes a detachable donning tab 5 which has a free end extending from cuff 2 and a non-free end fastened to cuff 2. Detachable donning tab 5 is coupled to cuff 2 on the inside surface at or in close proximity (collectively, "substantially near") to fold 3. Any object that can be grasped can be used as tab 5, including a tab, loop, appendage, etc. (collectively referred to as a "tab"). In one embodiment, sterile glove 20 is made with elastomeric impermeable material, such as latex, to prevent contamination.

In one embodiment, glove 20 is packaged in a sterile envelope which when opened presents glove 20 to the user palm up, with donning tab 5 located on the folded over cuff 2 and extending in the direction furthest away from the hand portion of the glove as shown in FIG. 2. Donning tab 5 extends sufficiently to allow the free end to be grasped without touching any other part of the glove. The user can grasp sterile glove 20 at the free end of donning tab 5 with a first hand, making it possible to insert the second hand into the finger portion of the glove. After the second hand is securely in the finger portion of the glove, donning tab 5 can be detached. In this manner, glove 20 is put on the second hand and no part of what remains has been touched or contaminated by the first hand. In one embodiment, glove 20 is contained in a dispenser adapted to maintain sterile conditions. Glove 20 in one embodiment is intended to be completely removed from its packaging or dispenser prior to donning.

Donning tab 5 can be located on cuff 2 by any known attachment mechanism that enables both a sufficiently strong attachment to allow glove 20 to be grasped firmly while inserting a hand and that also enables all, or at least the touched portion, of donning tab 5 to be subsequently detached. In one embodiment, donning tab 5 is attached to cuff 2 by an adhesive and includes, immediately adjacent to the glued area, perforations 6 that span all, or part of, the width of tab 5. Perforations 6 enable tab 5 when pulled in a suitable direction to tear away from the adhered area. This approach leaves a portion 7 of tab 5 still coupled to cuff 2 after tab 5 is torn away. Since portion 7 is located on the inside surface of cuff 2, when cuff 2 is fully unfolded and glove 20 is in use, portion 7 will be entirely on the inside of the cuff and will not interfere with the use of the glove. Further, once detachable tab 5 is removed, in one embodiment nothing is left on the outside of the glove that could interfere with the use of the glove or could provide a site for accumulation of contamination. In another embodiment, the entire tab 5 is detached from glove 20 by using a suitable releasable adhesive or a releasable fastener such as Velcro. In one embodiment, tab 5 is attached to cuff 2 in a manner that insures that the user cannot apply too much force to glove 20 while donning it to minimize risk of over stretching or tearing, thereby improving safety.

Figure 3:
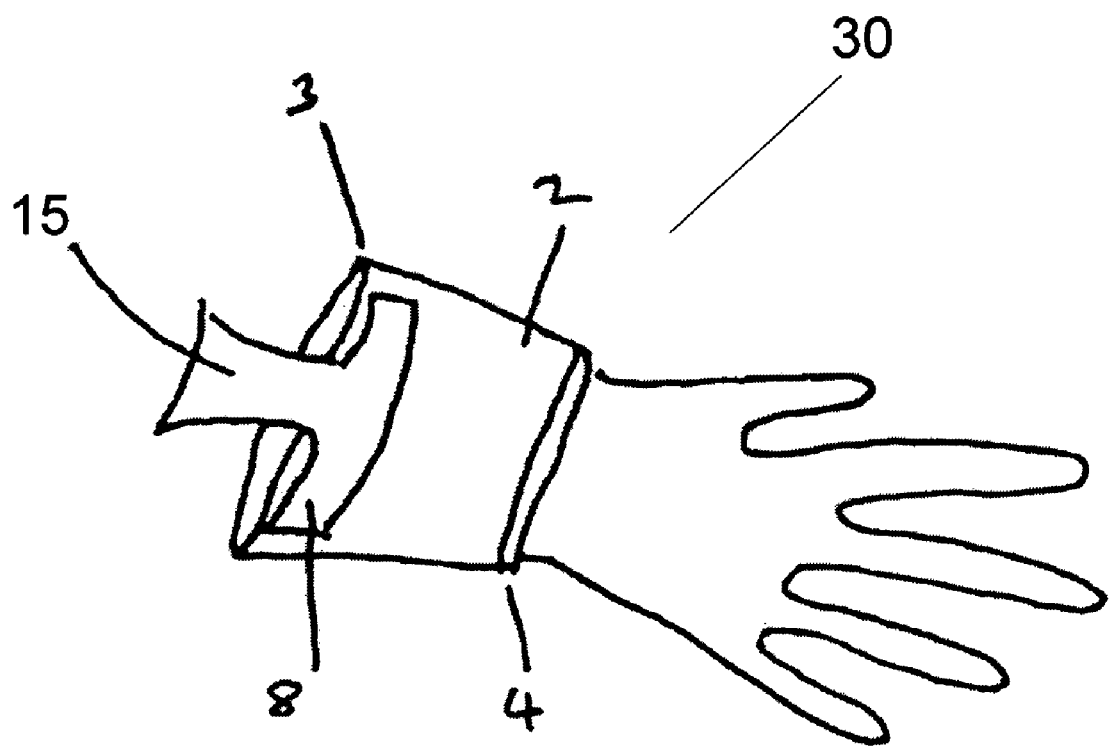
FIG. 3 is a perspective view of a sterile glove in accordance with another embodiment as it is configured when it is removed from packaging or other storage means and before being donned by a user.

FIG. 3 is a perspective view of a sterile glove 30 in accordance with another embodiment as it is configured when it is removed from packaging or other storage means such as a dispenser and before being donned by a user. Glove 30 includes a donning tab 15 attached to folded over cuff 2. Donning tab 15 has a non-free end 8 that is rigid or semi-rigid and is designed to support or stretch folded over cuff 2 in the area of fold 3 in an open position for easier insertion of a hand of a user. Non-free end 8 can be any shape or size that is convenient and promotes easy insertion of a hand.

Figure 4:
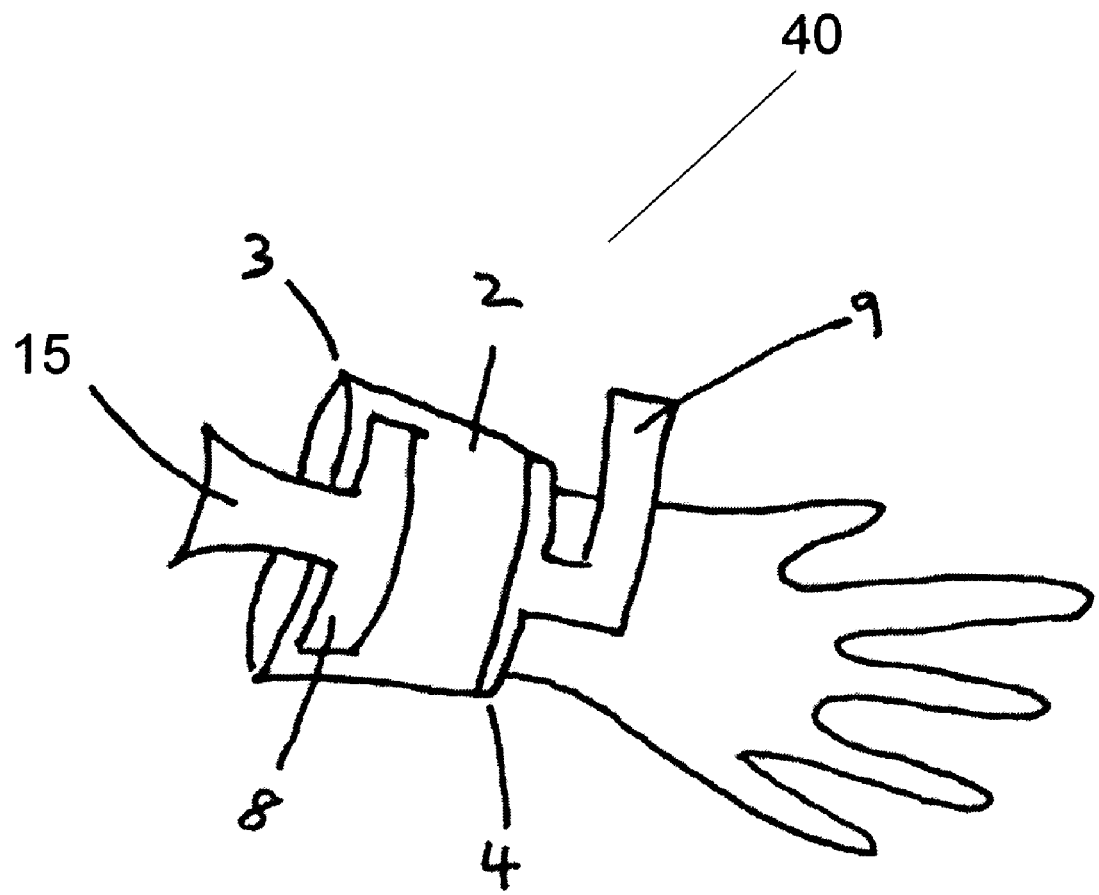
FIG. 4 is a perspective view of a sterile glove in accordance with another embodiment as it is configured when it is removed from packaging or other storage means and before being donned by a user.

FIG. 4 is a perspective view of a sterile glove 40 in accordance with another embodiment as it is configured when it is removed from packaging or other storage means and before being donned by a user. Sterile glove 40 is similar to sterile glove 30 but it includes an additional detachable tab 9 that can be used to unfold folded over cuff 2 without touching cuff 2 or any other part of glove 40, thus exposing the outside surface of cuff 2 without risk of contamination. In one embodiment, detachable tab 9 is located substantially near cuff rim 4. After a hand has been inserted into the finger portion of glove 40, detachable tab 9 can be grasped and pulled to unfold folded over cuff 2. Detachable tab 9 can then be detached using similar techniques as tab 5 of FIG. 2. In one embodiment, detachable tab 9 projects from the glove at a sufficient distance to allow the free end to be grasped without touching any other part of the glove. In one embodiment, at least a portion of detachable tab 9 is extended in a direction parallel to cuff rim 4, with this portion having sufficient length to make it possible to grasp the free end without contacting any other part of the glove.

Figure 5:
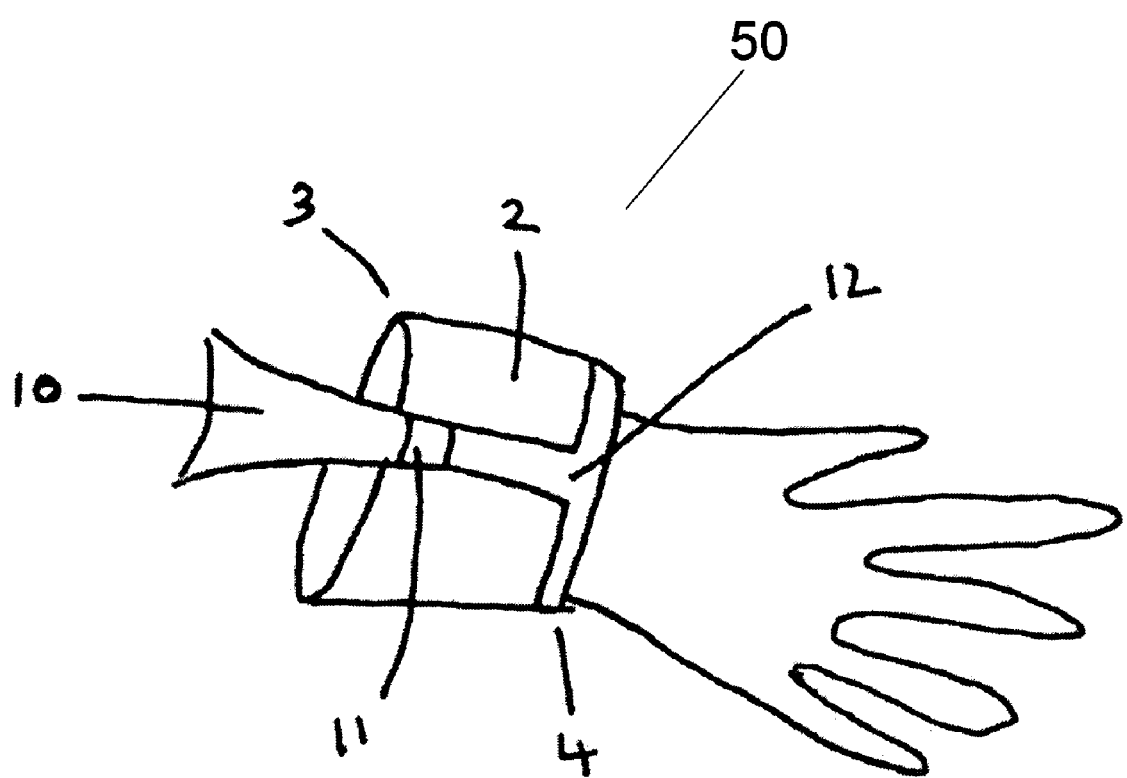
FIG. 5 is a perspective view of a sterile glove in accordance with another embodiment as it is configured when it is removed from packaging or other storage means and before being donned by a user.

FIG. 5 is a perspective view of a sterile glove 50 in accordance with another embodiment as it is configured when it is removed from packaging or other storage means and before being donned by a user. Sterile glove 50 includes a donning tab 10 attached to folded over cuff 2 at area 11 and area 12. Area 11 is in close proximity or substantially near to fold 3 and area 12 is in close proximity or substantially near to cuff rim 4. In another embodiment, area 12 is located at cuff rim 4. In donning glove 50, a user can grasp the glove with a first hand using the free end of donning tab 10, thereby enabling the second hand to be inserted into the finger portion of the glove. Once the second hand is in place, donning tab 10 can be separated from attachment area 11. At this point donning tab 10 is still attached to area 12 and therefore can be used to unfold folded over cuff 2. Tab 10 can then be separated from glove 50 at area 12.

Figure 6:
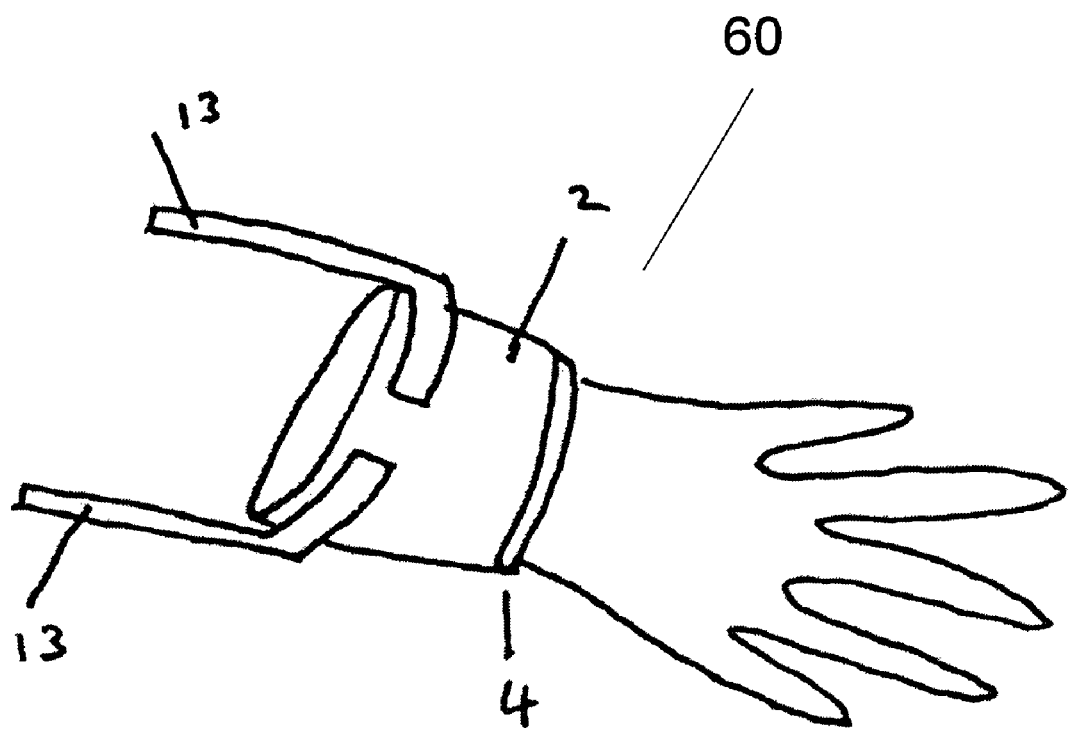
FIG. 6 is a perspective view of a sterile glove in accordance with another embodiment as it is configured when it is removed from packaging or other storage means and before being donned by a user.

FIG. 6 is a perspective view of a sterile glove 60 in accordance with another embodiment as it is configured when it is removed from packaging or other storage means and before being donned by a user. Sterile glove 60 includes two or more detachable donning tabs 13 that can be used to hold open cuff 2, enabling the user to more easily insert a hand. Detachable donning tabs 13 can be held by an assisting party or by a holding device, such as stationary stands or clamps. Because donning tabs 13 will be detached prior to use of the glove, the hands of the assisting party or the holding device does not need not be sterile.

As disclosed, sterile gloves in accordance with embodiments of the present invention include graspable and detachable donning tabs having a free end to assist the donning of the glove. The detachable tabs can be attached using any suitable method, including releasable adhesive, adhesive with a perforated tear-away section or releasable fasteners such as Velcro. The donning tabs can be of any shape or size that is convenient to use. For example a donning tab can have a hole or cut away in the free end, to enable more secure grasping. The donning tabs can be made of any suitable material or can be formed of the same material as the glove. Embodiments of the glove can be made from any suitable material. Since at least the touched parts of the donning tabs are detached prior to use of the glove, they can be used by non-sterile hands of either the glove user or an assisting party.

Several embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. A sterile glove comprising:
   a hand and finger portion;
   a cuff having an inside surface and an outside surface and a cuff rim, wherein the cuff is adapted to be folded over at a fold when the glove is packaged; and
   wherein a portion of the inside surface of the cuff becomes an outer facing surface when folded over;
   a first detachable tab coupled to the outer facing surface and comprising a free end, extending away from the finger portion when the cuff is folded over at the fold;
   wherein the first detachable tab comprises means for assisting in a donning of the glove and means for being substantially removed from the cuff after the glove has been donned.

2. The sterile glove of claim 1, wherein the first detachable tab is coupled substantially near the fold.

3. The sterile glove of claim 2, further comprising a second detachable tab coupled substantially near the cuff rim.

4. The sterile glove of claim 2, further comprising a second detachable tab coupled substantially near the fold on the inside surface of the cuff.

5. The sterile glove of claim 1, wherein the first detachable tab is coupled substantially near the cuff rim.

6. The sterile glove of claim 1, wherein the first detachable tab is coupled using a releasable adhesive.

7. The sterile glove of claim 1, wherein the first detachable tab is coupled using a releasable fastener.

8. The sterile glove of claim 1, wherein the first detachable tab comprises a perforated region that allows at least a portion of the first detachable tab to be detached from the cuff.

9. The sterile glove of claim 1, wherein the first detachable tab comprises a non-free end, and wherein the non-free end is rigid in order to hold the fold in an open position.

10. The sterile glove of claim 1, wherein the first detachable tab is coupled to the inside surface of the cuff.

11. The sterile glove of claim 1, further comprising a package adapted to contain the glove.

12. A method of packaging a sterile glove that comprises a hand and finger portion and a cuff having an inside surface, an outside surface and a cuff rim, the method comprising:
    folding the cuff at a fold so that at least a portion of the inside surface faces outward; and
    coupling a first detachable tab on the cuff, wherein the first detachable tab comprises a free end, wherein the first detachable tab is coupled to an outer facing surface of the cuff and extends away from the finger portion when the cuff is folded over at the fold;
    and wherein the first detachable tab is configured to assist in a donning of the glove and to be substantially removed from the cuff after the glove has been donned.

13. The method of claim 12, further comprising coupling the first detachable tab substantially near the fold.

14. The method of claim 13, wherein the first detachable tab comprises a non-free end that is rigid, further comprising holding the fold in an open position with the non-free end.

15. The method of claim 13, further comprising;
coupling a second detachable tab substantially near the cuff rim.

16. The method of claim 12, further comprising coupling the first detachable tab substantially near the cuff rim.

17. The method of claim 12, further comprising coupling the first detachable tab to the inside surface.

\* \* \* \* \*